United States Patent
Cutler

(10) Patent No.: US 6,194,433 B1
(45) Date of Patent: *Feb. 27, 2001

(54) SEXUAL DYSFUNCTION IN FEMALES

(75) Inventor: Neal R. Cutler, 10464 Sunset Blvd., Los Angeles, CA (US) 90077

(73) Assignee: Neal R. Cutler, Los Angeles, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/166,703

(22) Filed: Oct. 5, 1998

(51) Int. Cl.$^7$ .................................................... A61K 31/47
(52) U.S. Cl. .............................................................. 514/312
(58) Field of Search ........................................... 514/312

(56) References Cited

U.S. PATENT DOCUMENTS

| | | | |
|---|---|---|---|
| 1,897,423 | 2/1933 | Ferri . | |
| 2,584,166 | 2/1952 | Stevenson et al. | 167/64 |
| 2,696,209 | 12/1954 | Varaney | 128/132 |
| 3,373,746 | 3/1968 | White et al. | 128/294 |
| 4,311,707 | 1/1982 | Birnbaum et al. | 424/305 |
| 4,478,822 | 10/1984 | Haslam et al. | 424/78 |
| 4,610,868 | 9/1986 | Fountain et al. | 424/1.1 |
| 4,640,912 | 2/1987 | Hausman | 514/54 |
| 4,746,508 | 5/1988 | Carey et al. | 424/88 |
| 4,801,587 | 1/1989 | Voss | 514/248 |
| 4,829,991 | 5/1989 | Boeck | 128/79 |
| 5,011,931 | 4/1991 | MacLean et al. | 546/155 |
| 5,079,264 | 1/1992 | MacLean et al. | 514/629 |
| 5,270,323 | 12/1993 | Milne, Jr. et al. | 514/309 |
| 5,447,912 | 9/1995 | Gerstenberg et al. | 514/12 |
| 5,474,535 | 12/1995 | Place et al. | 604/60 |
| 5,492,911 | 2/1996 | Stief | 514/252 |
| 5,721,238 | * 2/1998 | Heiker et al. | 514/259 |
| 5,773,457 | * 6/1998 | Nahoum | 514/397 |
| 6,110,489 | * 8/2000 | Cutler | 424/449 |

FOREIGN PATENT DOCUMENTS

| | | | |
|---|---|---|---|
| 0 357 581 B2 | 7/1990 | (EP) | A61K/47/00 |
| 94/28902 | 12/1994 | (WO) . | |

OTHER PUBLICATIONS

Park et al., "Vasculogenic femal sexual dysfunction: The hemodynamic basis for vaginal engorgement insufficiency and clotoral erectile insufficiency," *Int. J. Impotence Res.*, 9:27–37 (1997).

McMurry, *Organic Chemistry*, 2nd Ed., Brooks/Cole Publishing, Belmont, CA (1988), pp. 1044–1045 and 1076.

Kelso, et al., "Actions of the Novel Vasodilator, Flosequinan, in Isolated Ventricular Cardiomyocytes," *J. Cardiovasc. Pharmacol.* 25:376–386 (1995).

Perreault, et al., "Differential inotropic effects of flosequinan in ventricular muscle from normal ferrets versus patients with end–stage heart failure," *Br. J. Pharmacol.* 106:511–516 (1992).

Jones, et al., "Effect of flosequinan on ischaemia–induced arrhythmias and on ventricular cyclic nucleotide content in the anaesthetized rat," *Br. J. Pharmacol.* 108:1111–1116 (1993).

Gristwood, et al., "Studies on the cardiac actions of flosequinan in vitro," *Br. J. Pharmacol.* 105:985–991 (1992).

Frodsham, et al., "Effect of flosequinan upon isoenzymes of phosphodiesterase from guinea–pig cardiac and vascular smooth muscle," *Eur. J. Pharmacol.* 211:383–391 (1992).

Garban et al., "Effect of aging on nitric oxide–mediated penile erection in rats," *Am. J. Phys.* 46:H467–H475 (1995).

Rajfer et al., "Nitric Oxide as a Mediator of Relaxation of the Corpus Cavernosum in Response to Nonadrenergic, Noncholinergic Neurotransmission," *New Engl. J. Med.* 326:90–94 (1992).

Boolel et al., "Sildenafil, a novel effective oral therapy for male erectile dysfunction," *Br. J. Ur.* 78:257–261 (1996).

Silver et al., "Differential pharmacologic sensitivity of cyclic nucleotide phosphodiesterase isozymes isolated from cardiac muscle, arterial and airway smooth muscle," *European J. Pharmacology*, 150:85–94 (1988).

Kauffman et al., "Characterization and Pharmacological Relevance of High Affinity Binding Sites for [$^3$H] LY186126, a Cardiotonic Phosphodiesterase Inhibitors, in Canine Cardiac Membranes," *Circulation Research*, 65(1):154–163.

Delcour et al., "Impotence: Evaluation with Cavernosography," *Radiology* 161:803–806(1986).

Porst et al., "Relevance of Dynamic Cavernosography to the Diagnosis of Venous Incompetence in Erectile Dysfunction," *J. Urol.* 137:1163–1167 (1987).

Lue et al., "Physiology of Erection and Pharmacological Management of Impotence," *J. Urol.* 37:829–836 (1987).

Malhotra et al., "Cavernosography in conjunction with artificial erection for evaluation of venous leakage in impotent men," *Radiology*, 161(3):799–802 (1986).

(List continued on next page.)

Primary Examiner—Theodore J. Criares
Assistant Examiner—Jennifer Kim
(74) *Attorney, Agent, or Firm*—Medlen & Carroll, LLP

(57) ABSTRACT

Methods for treating female erectile dysfunction are provided. The methods of the present invention comprise the utilization of pharmaceutical compositions to improve blood flow to sexual organs. The pharmaceutical compositions comprise quinolines and quinolones, as well as derivatives thereof.

18 Claims, No Drawings

OTHER PUBLICATIONS

Dawson et al., "Cilostazol has beneficial effects in treatment of intermittent claudication: results from a multicenter, randomized, prospective, double-blind trial," *Circulation*, 98(7):678–86 (1998).

Minami et al., "Inhibition of Shear Stree-Induced Platelet Aggregation by Cilostazol, A Specific Inhibitor of cGMP-Inhibited Phosphodiesterase, in vitro and ex-vivo," *Life Sciences*, 61(25):PL 383–389 (1997).

Shiraishi et al., "Effect of cilostazol a phosphodiesterase type III inhibitor, ON Histamine-induced increase in [$Ca^{2+}$]i and force in middle cerebral artery of the rabbit," *Br. J. Pharmacol.*, 123(5):869–878 (1997).

EMBASE abstract AN 97115666, Park, K. et al., 1997.*

Gristwood, R.W. et al., Br.J.Pharmacol., vol. 105, pp. 985–991, 1992.*

* cited by examiner

SEXUAL DYSFUNCTION IN FEMALES

FIELD OF THE INVENTION

The present invention relates to methods for improving blood flow and supply to female sexual organs, and more particularly, methods for the treatment of female erectile dysfunction. The methods of the present invention comprise the utilization of pharmaceutical compositions to induce erections in females having erectile dysfunction.

BACKGROUND

Females have sexual dysfunction. Post-menopausal women often complain of discomfort with intercourse, dryness of the vagina and diminished vaginal arousal. Studies comparing sexual dysfunction in couples have revealed 40% of the men had erectile or ejaculatory dysfunction whereas 63% of the women had arousal or orgasmic dysfunctions. Similar to male sexual dysfunction, the prevalence of female sexual dysfunction has been shown to increase with age and be associated with the presence of vascular risk factors and the development of the menopause.

The clitoris is the homologue of the penis. It is a cylindrical, erectile organ composed of the glans, corporal body and the crura. The corporal body is surrounded by a fibrous sheath, tunica albuginea, which encases cavernosal tissue consisting of sinusoids and surrounding smooth muscle. The clitoris responds to sexual excitement by tumescence and erection, although this does not occur with the degree of pressure elevation as found during penile erection. The characteristics of the clitoral blood flow, however, approximately parallel those of the male. See K. Park et al., "Vasculogenic female sexual dysfunction: The hemodynamic basis for vaginal engorgement insufficiency and clitoral erectile insufficiency," *Int. J Impotence Res.* 9:27 (1997).

Post-menopausal women and women with a history of vascular risk factors have been shown to have significantly more complaints of self-reported female vaginal and clitoral dysfunctions than pre-menopausal women or women without vascular risk factors. Such problems include, but are not limited to, atherosclerosis-induced vaginal engorgement insufficiency and clitoral erectile insufficiency syndromes.

What is needed is a pharmaceutical that is effective to treat such syndromes. Such pharmaceutical should lack in significant side effects.

SUMMARY OF THE INVENTION

The present invention relates to methods for improving blood flow and supply to female sexual organs, and more particularly, methods for the treatment of female erectile dysfunction. The methods of the present invention comprise the utilization of pharmaceutical compositions to induce erections in females having erectile dysfunction. The methods include treatment of female erectile dysfunction with quinolines and quinolones, including derivatives thereof. Quinolines and quinolones, including flosequinan, have pharmacological characteristics which improve blood flow and supply to female sexual organs.

It is not intended that the present invention be limited by the nature of the derivative. In one embodiment, the present invention contemplates halogenated quinolines (e.g., bromoquinoline) and isoquinolines (e.g., 1-methylisoquinoline and 5-nitroisoquinoline). In another embodiment, the present invention contemplates halogenated quinolones (e.g, flosequinolone). In a preferred embodiment, the quinolone is a thioquinolone or a sulphinyl or suphonyl derivatives thereof. In one embodiment, the halogenated quinolone is flosequinan (7-fluoro-1-methyl-3-methylsulphinyl-4-quinolone).

In one embodiment, the present invention contemplates a method, comprising: a) providing: i) a female with symptoms of sexual dysfunction, and ii) flosequinan; and b) administering said flosequinan to said female. It is not intended that the present invention be limited to particular symptoms of sexual dysfunction. A variety of such symptoms are contemplated, including but not limited to, poor blood flow to the sexual organs and/or failure to achieve orgasm. In one embodiment, the present invention contemplates administering said flosequinan to said female under conditions such that blood flow to the sexual organs of said female is improved.

In another embodiment, the method comprises providing: i) a female with erectile dysfunction, and ii) flosequinan; and introducing said flosequinan to said female such that a clitoral erection is produced.

It is not intended that the present invention be limited by the method of introduction of flosequinan. In one embodiment, the flosequinan is introduced into said female orally. In a preferred embodiment, the female is an adult human and the oral dosage is in a single dose per day of fifty to seventy-five milligrams. In other embodiments said flosequinan is introduced cutaneously, transurethrally, or by standard injection.

The present invention is not limited by the degree of response by the subject. In one embodiment, the erection induced is sufficient for normal stimulation.

It is not intended that the present invention be limited by the nature of the formulation. In one embodiment, the present invention contemplates a formulation comprising a quinoline or derivative thereof in a mixture comprising lactose.

Definitions

As used herein, the term "quinoline" refers to chemical compositions comprising quinoline as set forth in the following structure:

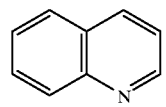

as well as other forms of quinoline, (e.g., isoquinoline):

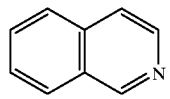

As used herein, the phrase "derivatives of quinoline" refers to chemical compositions comprising quinoline with a chemical group attached, including halogenated quinoline, e.g., 5-bromoquinolne:

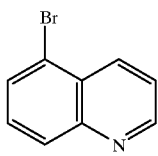

and 1-methylisoquinoline:

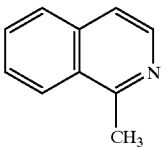

As used herein, the phrase "methylsulphinyl derivatives of quinoline" refers to chemical compositions comprising quinoline with a methylsulphinyl group attached. Examples include flosequinan (7-fluoro-1-methyl-3-methylsulphinyl-4-quinolone):

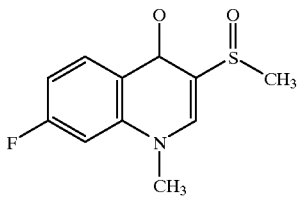

and sulfone metabolites of flosequinan:

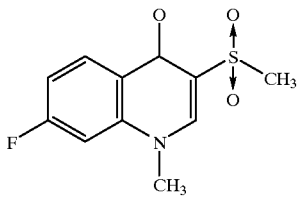

As used herein "standard injection" refers to the placement of a pharmaceutical composition into a subject (e.g., with a hypodermic needle). For example, such injection can be made subcutaneously, intravenously, intramuscularly, etc.

As used herein, "by oral administration" refers to the introduction of a pharmaceutical composition into a subject by way of the oral cavity (e.g., in aqueous liquid or solid form).

As used herein, "cutaneously" refers to the introduction of a pharmaceutical composition into a subject by application to the surface of the skin such that the composition is absorbed into the subject.

As used herein, "transurethrally" refers to the introduction of a pharmaceutical composition to the urethra of a subject such that the composition is absorbed into the subject.

As used herein "single dosage" refers to a pharmaceutical composition of a formulation that is capable of achieving its intended effect in a single application.

DETAILED DESCRIPTION OF THE INVENTION

The present invention contemplates the use of compositions that are effective to induce an erection in a human female suffering from lack of function of any origin, other than anatomical deficiencies (i.e., lacking a clitoris or a significant portion thereof) that preclude an erection. In particular, these compositions may be used to induce an erection in a female suffering from insufficiency caused by severe atherosclerosis. The compositions utilized in the methods of the present invention comprise quinolines and quinolones, including derivatives thereof.

While the present invention is not limited by the nature of the derivatives, in one embodiment, the present invention encompasses the use of a variety of quinoline derivatives (e.g., 5-bromoquinoline, 5-nitroisoquinoline, 8-nitroisoquinoline and 1-methylisoquinoline). One skilled in the art can readily produce such derivatives as set forth in McMurry, *Organic Chemistry* 2nd Ed., Brooks/Cole Publishing, Belmont, Calif. (1988), pages 1044–1045 and 1076.

In another embodiment, the present invention contemplates the use of methylthio and methylsulphinyl derivatives of quinoline. In a preferred embodiment, the methylsulphinyl derivative is flosequinan (7-fluoro-1-methyl-3-methylsulphinyl-4-quinolone).

Methods of producing methylsuphinyl and methylthio derivatives of quinoline, including flosequinan, are set forth in U.S. Pat. No. 5,079,264 and 5,011,931 to MacLean et al., hereby incorporated by reference. While it is not necessary to understand any particular mechanism to carry out the present invention, it is believed that in some circumstances flosequinan can act as a direct-acting vasodilator to relax the smooth muscle cells, which in turn increases blood flow.

The action of flosequinan in the body is not precisely understood. Its activity in the body is attributed to flosequinan itself, as well as its sulfone metabolite. It has been reported to be useful to some degree in the treatment of heart failure. [See Kelso et al., *J Cardiovasc. Pharmacol.* 25:376 (1995)]. However, its action appears to have little effect in patients with end-stage failure [Perreault et al., *Br. J Pharmacol.* 106:511 (1992)] and does not affect mortality or arrhythmias following coronary artery ligation [Jones et al., *Br. J. Pharmacol.* 108:1111 (1993)].

Likewise, flosequinan has been reported to be a selective inhibitor of phosphodiesterase III [Gristwood et al., *Br. J. Pharmacol.* 105:985 (1992)]. [Frodsham et al., *Eur. J. Pharmacol.* 211:383 (1992)], however, report that the phosphodiesterase inhibition of flosequinan, as relevant to its efficacy in heart failure, is questionable. Thus, the application of flosequinan to particular purposes in the body is not well-characterized and must be determined empirically.

Diagnosis of Female Erectile Dysfunction

Determination whether a human female is suffering from poor blood flow or supply is readily made by a person skilled in the art using a number of readily available diagnostic procedures. The human vagina receives arterial blood supply from the vaginal artery, the vaginal branch of the uterine artery, the internal pudendal artery, and the vaginal branches of the middle rectal artery. Blood flow in these areas can readily be assessed by a number of techniques. Arterial blood can be obtained and the blood levels of cholesterol and triglycerides can be analyzed as a first step. However, the preferred method is imaging.

While relatively non-invasive imaging is preferred, more invasive techniques can be used. For example, vaginal wall blood flow can be measured by laser Doppler flow probes placed into the vaginal muscularis layer within the spongy region of blood-filled spaces and vascular smooth muscle.

Clitoral intracavernosal erectile tissue blood flow can be measured with a similar laser Doppler flow probe placed into the corporal bodies. The flow probes are connected to a laser Doppler flowmeter (Transonic Systems, Inc.) which is calibrated against an internal standard reading flow in units of ml/min/100 gm of tissue.

The laser Doppler probe uses the Doppler shift of a projected beam of laser light that registers on a photodetector. Static tissues will produce no Doppler shift in wavelength but moving red blood cells will produce a shift proportional to the red cell velocity.

Treatment of Female Erectile Dysfunction

It is not intended that the present invention be limited by the particular nature of the therapeutic preparation. For example, the quinolines or quinolone derivatives (e.g., flosequinan) can be provided together with physiologically tolerable liquid, gel or solid carriers, diluents, adjuvants and excipients. In addition, quinoline or quinolone analogs may be used together with other chemotherapeutic agents. On the other hand, formulations may also contain such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%–95% of active ingredient, preferably 2%–70%.

The present invention is not limited by the method of introduction of the therapeutic compound to the body. Among other methods, the present invention contemplates administering cutaneously, orally, transurethrally or by standard injection.

Oral administration of flosequinan is effective, with a mean absolute bioavailability of 72% following a single does of fifty milligrams. Peak plasma concentrations of flosequinan are observed 1–2 hours following oral administration, while peak metabolite plasma levels are observed about seven hours following oral dosage. While the present invention is not limited to a specific dosage level, for adult humans, in one embodiment the dosage is a single dosage per day of 50 milligrams, while in another embodiment the dosage is a single dosage per day of 75 milligrams.

Flosequinan is water soluble and is soluble in many organic solvents. Thus, while the present invention is not limited by the form of oral administration, aqueous and organic solution of flosequinan for oral administration is contemplated. Likewise, flosequinan can be associated with a solid pharmaceutical carrier for solid oral administration (i.e., in pill form). One skilled in the art is able to readily prepare such solid formulations, and in one embodiment, the inactive ingredients include croscarmellose sodium, hydroxypropyl methylcellulose, lactose, magnesium stearate, methocel E5, microcrystalline cellulose, povidine, propylene glycol and titanium dioxide.

Flosequinan may also be administered cutaneously in a carrier adapted for topical administration. Such carriers include creams, ointments, lotions, pastes, jellies, sprays, aerosols, bath oils, or other pharmaceutical carriers which accomplish direct contact between flosequinan and the pore of the skin. In general pharmaceutical preparations may comprise from about 0.001% to about 10%, and preferably from about 0.01 to 5% by w/w of the active compound (e.g., flosequinan) in a suitable carrier. In some cases it may be necessary to dissolve the flosequinan in an appropriate solvent such as ethanol or DMSO (dimethylsulfoxide), and the like, to facilitate incorporation into a pharmaceutical preparation. Likewise, the present invention can be incorporated in other products associated with sexual activity.

The present invention is not limited by a particular method for introducing flosequinan transurethrally. In one embodiment, flosequinan is introduced to the urethra in a carrier as described for cutaneous administration. Devices and methods for transurethral introduction of pharmaceutical compositions is described in U.S. Pat. No. 5,474,535 to Place et al.; Voss, U.S. Pat. No. 4,801,587 and Kock, EPA 0357581, all hereby incorporated by reference.

Additional methods of introducing flosequinan transurethrally include the use of medicated catheters, such as those used to prevent or treat localized infections and irritation of the urethra and bladder (See U.S. Pat. No. 4,640,912, hereby incorporated by reference). Alternatively, transurethral administration of pharmaceutical compositions is presented in U.S. Pat. Nos. 4,478,822, 4,610,868, 4,640,912 and 4,746,508, all hereby incorporated by reference, and medicated urethral suppositories, inserts or plugs, typically containing anti-infective agents or spermicide are disclosed in U.S. Pat. Nos. 1,897,423, 2,584,166, 2,696,209 and 3,373,746, all incorporated by reference.

Among the physiologically acceptable compositions for use in the methods is physiological saline or phosphate buffered saline, in which flosequinan is dissolved or suspended. Such a physiologically acceptable composition can also include a non-irritant preservative, such as, e.g., benzalkonium chloride at 0.05% (w/v) to 0./2% (w/v). As the skilled artisan will understand, there are numerous non-toxic salts of VIP, PHM and α-adrenergic blockers that can be employed in a physiologically acceptable composition for use in the methods herein, including, among others, the chloride, bromide, acetate, sulfate, and mesylate salts. While the present invention is not limited to the method of injecting flosequinan, in the preferred embodiment, it is injected with a standard syringe.

In one embodiment, the administration of the compositions of the present invention is accompanied by sexual stimulation to induce an erection. The sexual stimulation can begin before or after the introduction of flosequinan. If the stimulation begins after the injection, it is preferably begun within 5 to 10 minutes to insure that there is significant overlap of the pharmacological effects of the pharmaceutical composition administered and the stimulative effects of the sexual stimulation.

From the above, it should be clear that the present invention provides methods of treatment of female erectile dysfunction with pharmaceutical agents. In particular, quinolines and quinolones are administered therapeutically to patients having such dysfunction.

What is claimed is:

1. A method of treating female sexual dysfunction, comprising:
 a) providing:
  i) a female with symptoms of sexual dysfunction, and
  ii) flosequinan; and
 b) administering said flosequinan to said female.

2. The method of claim 1, wherein said flosequinan is administered by oral administration.

3. The method of claim 1, wherein said female is an adult human and said oral administration is of fifty to seventy-five milligrams of said flosequinan.

4. The method of claim 1, wherein said flosequinan is administered cutaneously.

5. The method of claim 1, wherein said flosequinan is administered transurethrally.

6. The method of claim 1, wherein said administering step further comprises administering said flosequinan in pill form.

7. The method of claim 1, wherein sexual stimulation is additionally provided.

8. The method of claim 1, wherein said flosequinan comprises an inactive ingredient selected from the group consisting of croscarmellose sodium, hydroxypropyl methylcellulose, methylcellulose, povidine, propylene glycol and titanium dioxide.

9. The method of claim 1, wherein said flosequinan is formulated with a carrier, wherein said carrier provides direct contact between said flosequinan and the pore of the skin.

10. The method of claim 9, wherein said carrier is selected from the group consisting of creams, ointments, lotions, pastes, jellies, sprays, aerosols, and bath oils.

11. The method of claim 1, wherein said flosequinan is formulated with additives selected from the group consisting of binders, fillers, carriers, preservatives, stabilizing agents, emulsifiers, buffers and excipients.

12. The method of claim 11, wherein said excipient is selected from the group consisting of mannitol, lactose, starch, magnesium stearate, sodium saccharin, cellulose and magnesium carbonate.

13. The method of claim 1, wherein said flosequinan is administered by injection.

14. The method of claim 1, wherein said symptoms comprise diminished blood flow to the sexual organs of said female.

15. The method of claim 1, wherein said symptoms comprise clitoral erection dysfunction.

16. The method of claim 1, wherein said flosequinan is administered to said female with symptoms of sexual dysfunction prior to sexual stimulation.

17. The method of claim 1, wherein said flosequinan is administered to said female with symptoms of sexual dysfunction concurrent with sexual stimulation.

18. The method of claim 1, wherein said flosequinan is administered to said female with symptoms of sexual dysfunction upon cessation of sexual stimulation.

* * * * *